US00PP24883P3

(12) United States Plant Patent
Leelachaikul

(10) Patent No.: US PP24,883 P3
(45) Date of Patent: Sep. 16, 2014

(54) *ADENIUM* PLANT NAMED 'LEELADE204'

(50) Latin Name: *Adenium obesum*
Varietal Denomination: LEELADE204

(76) Inventor: Anong Leelachaikul, Bangkok (TH)

( * ) Notice: Subject to any disclaimer, the term of this patent is extended or adjusted under 35 U.S.C. 154(b) by 33 days.

(21) Appl. No.: 13/573,445

(22) Filed: Sep. 15, 2012

(65) Prior Publication Data

US 2014/0082784 P1 Mar. 20, 2014

(51) Int. Cl.
*A01H 5/00* (2006.01)

(52) U.S. Cl.
USPC ..... Plt./226

(58) Field of Classification Search
USPC ..... Plt./263.1, 226, 373
See application file for complete search history.

*Primary Examiner* — Kent L Bell
(74) *Attorney, Agent, or Firm* — Cassandra Bright

(57) ABSTRACT

A new and distinct *Adenium* cultivar named 'LEELADE204' is disclosed, characterized by unique double, deep red flowers. The new variety is a *Adenium*, typically produced as an indoor ornamental plant.

1 Drawing Sheet

Latin name of the genus and species: *Adenium obesum.*
Variety denomination: 'LEELADE204'.

BACKGROUND OF THE INVENTION

This application relates to a new cultivar of *Adenium obesum*. The new variety is the product of a planned breeding program. The new variety originated as a seedling from the crossing of the unpatented, proprietary seed parent *Adenium obesum* 'VCKRR1' with the unpatented, proprietary pollen parent referred to as *Adenium obesum* 'VKGR7'. The crossing was made by the inventor in a non-commercial nursery during 2006.

The new variety was first selected by the inventor, Anong Leelachaikul, a citizen of Thailand, in October 2008, at the same nursery in Bangkok, Thailand. After identifying the new variety as a potentially interesting selection, the inventor continued confidential testing arid propagation of 'LEELADE204', assessing stability of the unique characteristics of this variety.

Asexual reproduction of the new cultivar 'LEELADE204' was first performed in October 2009, at a commercial nursery in Bangkok, Thailand by taking a nodal cutting from the new variety and grafting that to a rootstock plant. The rootstock plants are started from seed, and are unnamed, unpatented, varieties of *Adenium obesum*. Access to all plants was restricted, as plants were kept in a greenhouse not open to the public. Through subsequent propagation by vegetative cuttings, multiple generations have been reproduced, which have shown that the unique features of this cultivar are stable and reproduced true to type.

SUMMARY OF THE INVENTION

The cultivar 'LEELADE204' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LEELADE204'. These characteristics in combination distinguish 'LEELADE204' as a new and distinct *Adenium* cultivar:

1. Double flowers.
2. Deep red flowers

PARENT COMPARISON

Plants of the new cultivar 'LEELADE204' are similar to the seed parent, *Adenium* 'VCKRR1' in most horticultural characteristics. The new variety, however, produces double layered flowers whereas the seed parent produces single layered flowers.

Plants of the new cultivar 'LEELADE204' are similar to the pollen parent, *Adenium* 'VKGR7' in most horticultural characteristics. The new variety, however, produces flowers in a different color of red, than the pollen parent 'VKGR7'.

COMMERCIAL COMPARISON

Plants of the new cultivar 'LEELADE204' are similar to the commercial variety, *Adenium* 'Sup Jaroen' in most horticultural characteristics. However, the new variety differs in the following characteristics:

1. Different leaf share and color
2. Different petal shape

Plants of the new cultivar 'LEELADE204' are similar to the commercial variety, *Adenium* 'Valentine Rose' in most horticultural characteristics. However, the new variety differs in the following characteristics:

1. Different red flower color
2. Different leaf shape and color.

BRIEF DESCRIPTION OF THE PHOTOGRAPH

The accompanying photograph in FIG. 1 illustrates in full color a typical plant of 'LEELADE204' grafted outdoors in Thailand and grown in a commercial greenhouse in Honselersdijk, the Netherlands. This plant is approximately 9 months old from the graft, shown planted in 15 cm. container. The plant has been grown according to the details in the following paragraph. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2001, except where general terms of ordinary dictionary significance are used. The following observations and measurements describe 'LEELADE204' plants grown according to the following protocols.

Taking place in a commercial nursery, outdoors in Bangkok, Thailand, rootstock is grown from seeds. Seeds are planted and grown for 12-14 months. After that, heads are taken off the rootstock plants and the plants are grafted together with the selected variety.

Grafting is done by means of taking a nodal cutting from the candidate variety and placing that on top of the cut of the rootstock plant. Immediately after that, the top of the plant is covered by a layer of plastic and tied down by a rubber band. The plastic covers the actual graft entirely.

Rootstock plants during the first few weeks after seeding are grown under shade, and after that they are grown in Thailand in full sun. Stock plants of the candidate variety, resulting in the nodal cutting are also grown in Thailand in full sun.

During and until 1-2 weeks after grafting, plants are placed in a greenhouse that has both shade cloth and overhead plastic. This protects the grafted plants against the sun and the rain. After that, the grafted plants are placed in full sun again.

Three to four months after grafting, the grafted plants are cut back and shipped to the Netherlands. In the Netherlands, the plants continue to grow for 3-5 months, after which they are sold as flowering plant. Therefore, counted from the date of grafting, it takes 6-9 months to produce a finished flowering plant.

In Thailand the plants grow under natural conditions, with temperatures ranging approximately from 10° C. to 40° C., and very bright sunlight. In the Netherlands, the plants are grown in a greenhouse with average day temperature about 26 degrees Celsius and average night temperature about 22 degrees Celsius, un-shaded, to allow as much natural light as possible.

Measurements and numerical values below represent averages of typical plant types.

Botanical classification: *Adenium obesum* 'LEELADE204'.

PROPAGATION

Root description: The plant described is grafted and does not have its own roots for description.

PLANT

Caudex description:
- *Diameter*.—Average: 4.5 cm.
- *Height*.—Average: 20.5 cm.
- *Color*.—Greyed-green, near RHS 195A to 196B.
- *Texture*.—Smooth, very slightly glossy.

Plant spread: Approximately 25.6 cm.

Plant height: Top of flowering plane, average: 41.0 cm. Top of foliar plane, average: 41.0 cm.

Growth rate: Moderate.

Length of primary stem: Approximately 3.0 cm.

Diameter of primary stem: Approximately 1.5 cm.

Stem color: Greyed-green, in between near RHS 191A and 198A.

Stem texture: Smooth, very slightly glossy.

Lateral branches:
- *Quantity*.—3 (after pinching).
- *Length*.—9.7 cm.
- *Diameter*.—0.7 cm.
- *Color*.—Green, near RHS 143B, older stems colored greyed-green, in between near RHS 191A and 198A. Texture/Pubescence: Smooth, moderately glossy.

Internode length: Approximately 0.6 cm.

Age of plant described: Approximately 6 to 9 months from grafting onto a 12 month old rootstock. Grafted plants grown in the Netherlands, in a commercial greenhouse.

FOLIAGE

Leaf:
- *Arrangement*.—Alternate.
- *Quantity*.—Approximately 20 per lateral branch.
- *Average length*.—Approximately 9.2 cm.
- *Average width*.—Approximately 3.9 cm.
- *Shape of blade*.—Oblanceolate.
- *Apex*.—Abruptly acute.
- *Base*.—Narrow cuneate.
- *Attachment*.—Sessile.
- *Margin*.—Entire.
- *Texture of top surface*.—Smooth, glossy.
- *Texture of bottom surface*.—Smooth, matte.
- *Pubescence*.—No pubescence.
- *Color*.—Young foliage upper side: Green, near RHS 143B. Young foliage under side: Green, near in between RHS 138B and 143C. Mature foliage upper side: Green, near RHS N137D. Mature foliage under side: Green, near RHS 138B.
- *Venation*.—Type: Pinnate. Venation color upper side: Greyed-green, near RHS 192C. Venation color under side: Greyed-green, near RHS 192A.
- *Petiole*.—No petioles present, leaves sessile.

FLOWERING CHARACTERISTICS

Natural flowering season: In Thailand, the plants flower all year around, but during heavy rain periods, the plants do drop most or all of their flowers. Therefore, especially during the rainy seasons in Thailand, the plants will not flower so heavily as during the dry seasons. In the Netherlands, the plants will naturally flower most heavily during periods of very heavy sun and long days, particularly in July and August and to a lesser extent in June and September.

Inflorescence type and habit: Axillary compound cyme.

Flower Longevity on plant: Average: After fully opening, the flowers will stay on the plant on average between 5-10 days.

Quantity of flowers: About 9 buds and 3 fully opened flowers per plant, at one time.

Inflorescence size:
- *Diameter*.—Approximately 15.7 cm.
- *Height*.—Approximately 11.0 cm.

Individual flower size:
- *Diameter*.—Average: 8.1 cm.
- *Flower tube length*.—Average: 4.2 cm.
- *Flower tube diameter at distal end*.—Average: 2.0 cm.

*Flower tube diameter at proximal end*.—Average: 0.6 cm.

Petals:

*Petal arrangement*.—Rotate.

*Length from throat*.—Average: 4.1 cm.

*Width*.—Average: 3.5 cm.

*Quantity*.—Average: 5.

*Texture*.—Smooth, slightly velvety, dull.

*Margin*.—Entire.

*Tip shape*.—Unequal emarginate.

*Petaloids*.—Average: 10, average length from throat: 4.3 cm, average width: 3.8 cm, texture: smooth, slightly velvety, dull, margins entire, tip shaped abruptly acute to rounded.

Color:

*Petals*.—When opening: Upper surface: Red-purple, near RHS 60A, with a narrow longitudal stripe colored white, RHS N155C, base lighter red-purple, RHS 63C, outer margins red; RHS 53A. Lower surface: Red-purple, near RHS N57D, with a narrow longitudal stripe colored white, RHS N155C, outer margins red-purple, RHS 58A. Fully opened: Upper surface: Red to red-purple, in between near 60A, base lighter; RHS 61B. Lower surface: Red-purple, near RHS N57D, outer margins red-purple, RHS 58A. Flower throat (inside): White, near RHS 155A. Flower throat, vein: White, near RHS 155A. Flower tube (outside): Green-yellow, near RHS 1D. Flower tube, vein: Red-purple, near RHS N57A. Fading: Petals fading to: Red-purple, near RHS 60A.

Color:

*Petaloids*.—When opening: Upper surface: Red, near RHS 53A, base lighter red to red-purple; in between RHS 53C and N57A, outer margins red, slightly darker than RHS 53A. Lower surface: Red-purple, near RHS N57C, base lighter; RHS 63C, outer margins red, RHS 53B. Fully opened: Upper surface: Red-purple, near RHS N57A, base lighter; RHS N57D, outer margins red to red-purple, in between near RHS 53A and 60A. Lower surface: Red-purple, near RHS N57D, lighter towards the base; 62B, outer margins red-purple, RHS 59D. Fading Petaloids fading to: Not fading.

Bud:

*Shape*.—Oblanceolate.

*Length*.—Average: 2.9 cm.

*Diameter*.—Average: 1.2 cm.

*Color*.—Yellow-green, near RHS 145B, top red, RHS 53D.

Peduncle:

*Length*.—Average: 0.9 cm.

*Diameter*.—Average; 0.4 cm.

*Color*.—Green, near RHS 143B.

*Orientation*.—Outward.

*Strength*.—Moderately strong.

Pedicel:

*Length*.—Average: 1.3 cm.

*Diameter*.—Average: 0.4 cm.

*Color*.—Yellow-green, near RHS 144B.

*Orientation*.—Outward to upright.

*Strength*.—Moderately strong.

Sepals:

*Quantity per flower*.—Average: 5.

*Shape*.—Narrow ovate.

*Length*.—Approximately 0.9 cm.

*Width*.—Approximately 0.4 cm.

*Margin*.—Entire.

*Texture*.—Smooth.

*Color*.—Upper and lower surfaces Yellow-green; near RHS 145B.

*Apex*.—Mucronulate.

REPRODUCTIVE ORGANS

Stamens:

*Number*.—Average: 10.

*Filament length*.—Approximately 0.4 cm.

Anthers:

*Shape*.—Linear.

*Length*.—Approximately 2.9 cm.

*Color*.—Red-purple, near RHS 62C.

*Pollen*.—Color: No pollen detected. Quantity: No pollen detected.

Pistil:

*Number*.—Average: 1.

*Length*.—Approximately 1.8 cm.

*Style*.—Length: Approximately 1.75 cm. Color: Yellow-green, near RHS 145A to 145B.

*Stigma*.—Shape: Club-shaped. Color: Yellow-green, near. RHS 145B. Ovary color: Yellow-green, near RHS 144B.

OTHER CHARACTERISTICS

Disease resistance: Good resistance to the normal diseases found in *Adenium*.

Drought tolerance and cold tolerance: Normal for species, USDA zone 10 and higher.

Fruit/seed production: No fruits/seeds detected to date.

What is claimed is:

1. A new and distinct cultivar of *Adenium* plant named 'LEELADE204' as herein illustrated and described.

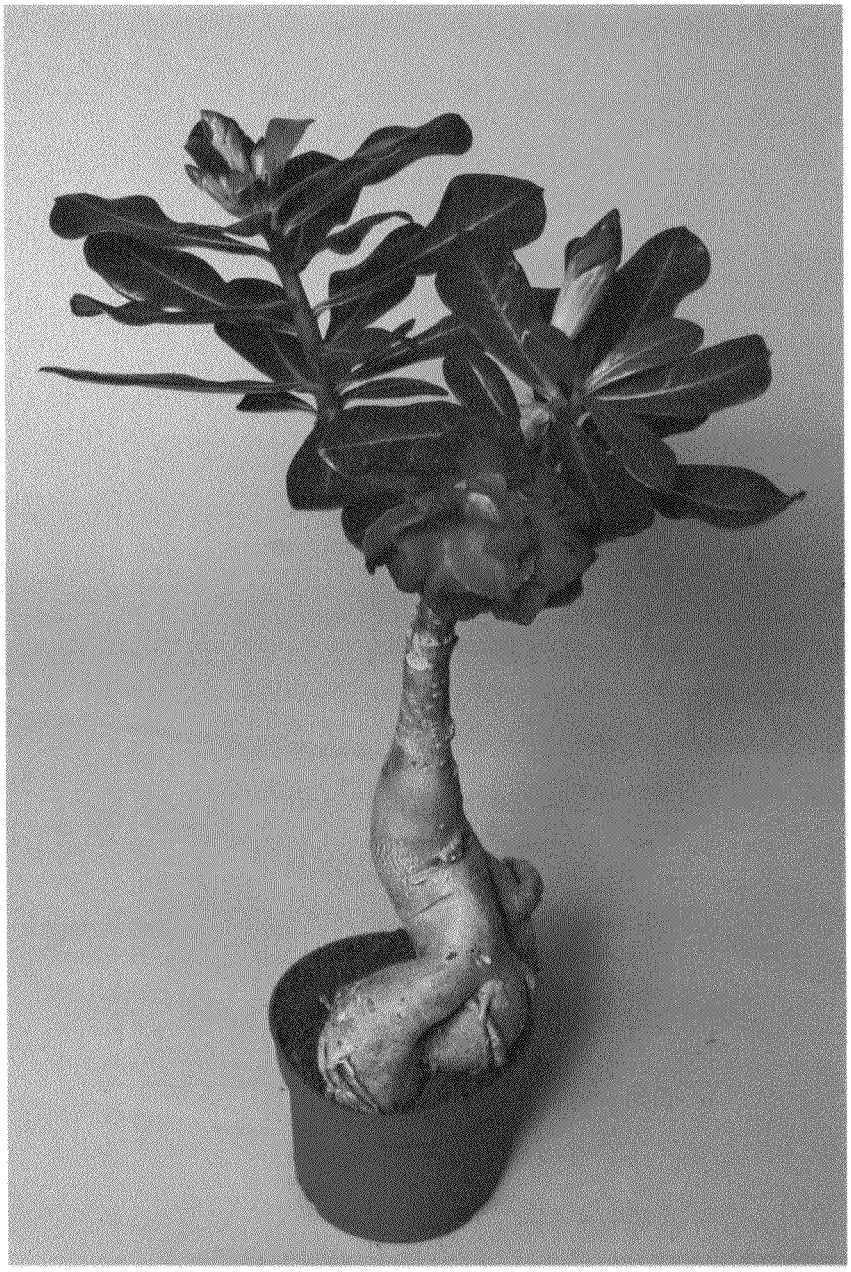

* * * * *